US011324863B2

(12) United States Patent
Nagale et al.

(10) Patent No.: US 11,324,863 B2
(45) Date of Patent: *May 10, 2022

(54) METHODS AND KITS FOR PROVIDING SUPPORT TO PELVIC TISSUE

(71) Applicant: Boston Scientific Scimed, Inc., Maple Grove, MN (US)

(72) Inventors: Sandra Nagale, Bolton, MA (US); Mark W. Boden, Harrisville, RI (US); Andrew Dolan, Bridgewater, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/168,583

(22) Filed: Feb. 5, 2021

(65) Prior Publication Data

US 2021/0162100 A1   Jun. 3, 2021

Related U.S. Application Data

(63) Continuation of application No. 16/504,655, filed on Jul. 8, 2019, which is a continuation of application (Continued)

(51) Int. Cl.
| | |
|---|---|
| *A61L 31/16* | (2006.01) |
| *A61K 9/00* | (2006.01) |
| *A61L 31/04* | (2006.01) |
| *A61L 31/06* | (2006.01) |
| *A61L 27/52* | (2006.01) |

(Continued)

(52) U.S. Cl.
CPC .......... *A61L 31/16* (2013.01); *A61K 9/0034* (2013.01); *A61L 27/52* (2013.01); *A61L 27/54* (2013.01); *A61L 31/042* (2013.01); *A61L 31/044* (2013.01); *A61L 31/045* (2013.01); *A61L 31/047* (2013.01); *A61L 31/048* (2013.01); *A61L 31/06* (2013.01); *A61L 31/145* (2013.01); *A61L 2400/06* (2013.01)

(58) Field of Classification Search
CPC ........ A61L 31/16; A61L 31/145; A61L 27/52; A61L 27/54; A61L 31/042; A61L 31/044; A61L 31/045; A61L 31/047; A61L 31/048; A61L 31/06; A61L 2400/06
See application file for complete search history.

(56) References Cited

U.S. PATENT DOCUMENTS

| | | | |
|---|---|---|---|
| 6,165,201 | A | 12/2000 | Sawhney et al. |
| 6,319,260 | B1 | 11/2001 | Yamamoto |
| (Continued) | | | |

FOREIGN PATENT DOCUMENTS

WO   2013077357 A1   5/2013

*Primary Examiner* — Carlos A Azpuru
(74) *Attorney, Agent, or Firm* — Seager, Tufte & Wickhem, LLP

(57) ABSTRACT

In some aspects, the present invention provides surgical procedures that comprise applying compositions into and/or onto pelvic tissue to provide support to the pelvic tissue. The injectable hydrogel composition comprises a polysaccharide. In embodiments, the polysaccharide comprises one or more of a glycosaminoglycan, chitosan, hyaluronic acid, dextran, alginic acid and hydroxyethyl starch. In other aspects, the present disclosure pertains to kits that are useful for performing such procedures.

17 Claims, 2 Drawing Sheets

Related U.S. Application Data

No. 15/599,166, filed on May 18, 2017, now Pat. No. 10,376,616, which is a continuation of application No. 14/138,733, filed on Dec. 23, 2013, now Pat. No. 9,682,177.

(60) Provisional application No. 61/746,711, filed on Dec. 28, 2012.

(51) Int. Cl.
  *A61L 27/54*  (2006.01)
  *A61L 31/14*  (2006.01)

(56) References Cited

U.S. PATENT DOCUMENTS

| | | |
|---|---|---|
| 6,514,534 B1 | 2/2003 | Sawhney |
| 6,632,457 B1 | 10/2003 | Sawhney |
| 6,818,018 B1 | 11/2004 | Sawhney |
| 7,963,287 B2 | 6/2011 | Lanphere et al. |
| 9,216,188 B2 * | 12/2015 | Zeitels ................... C08J 3/246 |
| 9,682,177 B2 * | 6/2017 | Nagale .................. A61L 31/145 |
| 2001/0046518 A1 | 11/2001 | Sawhney |
| 2002/0082636 A1 | 6/2002 | Sawhney et al. |
| 2002/0106409 A1 | 8/2002 | Sawhney et al. |
| 2003/0012734 A1 | 1/2003 | Pathak et al. |
| 2004/0094162 A1 | 5/2004 | Noyes |
| 2006/0070631 A1 | 4/2006 | Scopton et al. |

* cited by examiner ns pplication is a continuation of Ser. No. 16/504,655,

METHODS AND KITS FOR PROVIDING SUPPORT TO PELVIC TISSUE

CROSS-REFERENCE TO RELATED APPLICATIONS

This application is a continuation of Ser. No. 16/504,655, filed on Jul. 8, 2019, which is a continuation of U.S. patent application Ser. No. 15/599,166, filed on May 18, 2017, which is a continuation of U.S. patent application Ser. No. 14/138,733, filed on Dec. 23, 2013, which is now granted as U.S. Pat. No. 9,682,177, which claims the benefit of priority under 35 U.S.C. § 119 to U.S. Provisional Application Ser. No. 61/746,711, filed on Dec. 28, 2012, the disclosures of which are incorporated by reference herein in their entirety.

FIELD OF THE INVENTION

The present invention relates to procedures, compositions and kits pertaining to surgical repair.

BACKGROUND OF THE INVENTION

Medical surgical procedures are known in which various ligaments, connective tissue, muscles and organs of the body are repaired.

As a specific example, common surgical repairs for pelvic organ prolapse (POP) include those whereby biologic or synthetic grafts are used to provide support for the prolapsed organs. Currently available graft materials can be less than ideal for this purpose. For example, biologic grafts commonly lack ability to provide the required strength for organ support, although they are better integrated with tissue than synthetic grafts. Synthetic meshes may result in complications such as mesh erosion, dyspareunia, and infection. In either type of repair, the ligaments originally used to hold the vagina and uterus are often too weak for use in organ repair (e.g., re-suspension of the vaginal apex). Instead, alternative ligaments such as sacrospinous ligament (which extends from the sacrum to its insertion on the ischial spine) are used to attach the new grafts. The consequences of this approach include (1) an altered anatomic position of the affected organs and (2) altered tissue biomechanics that occur due to increased tension between the organ(s) and the non-native ligaments (now connected by a foreign material with biomechanical properties different than native tissue).

Deficiencies in these and other surgical procedures may be addressed using the procedures, compositions and kits described herein.

SUMMARY OF THE INVENTION

In some aspects, the present invention provides surgical procedures that comprise applying compositions into and/or onto tissue, including supporting tissues (e.g., ligaments, connective tissue, muscles, etc.) for pelvic organs, among other tissues.

In other aspects, the present invention pertains to compositions that are useful for performing such procedures, among others.

In still other aspects, the present invention pertains to kits that are useful for performing such procedures, among others.

These and various additional aspects, embodiments and advantages of the present invention will become immediately apparent to those of ordinary skill in the art upon review of the Detailed Description and any appended claims to follow.

DETAILED DESCRIPTION

Figure 1:
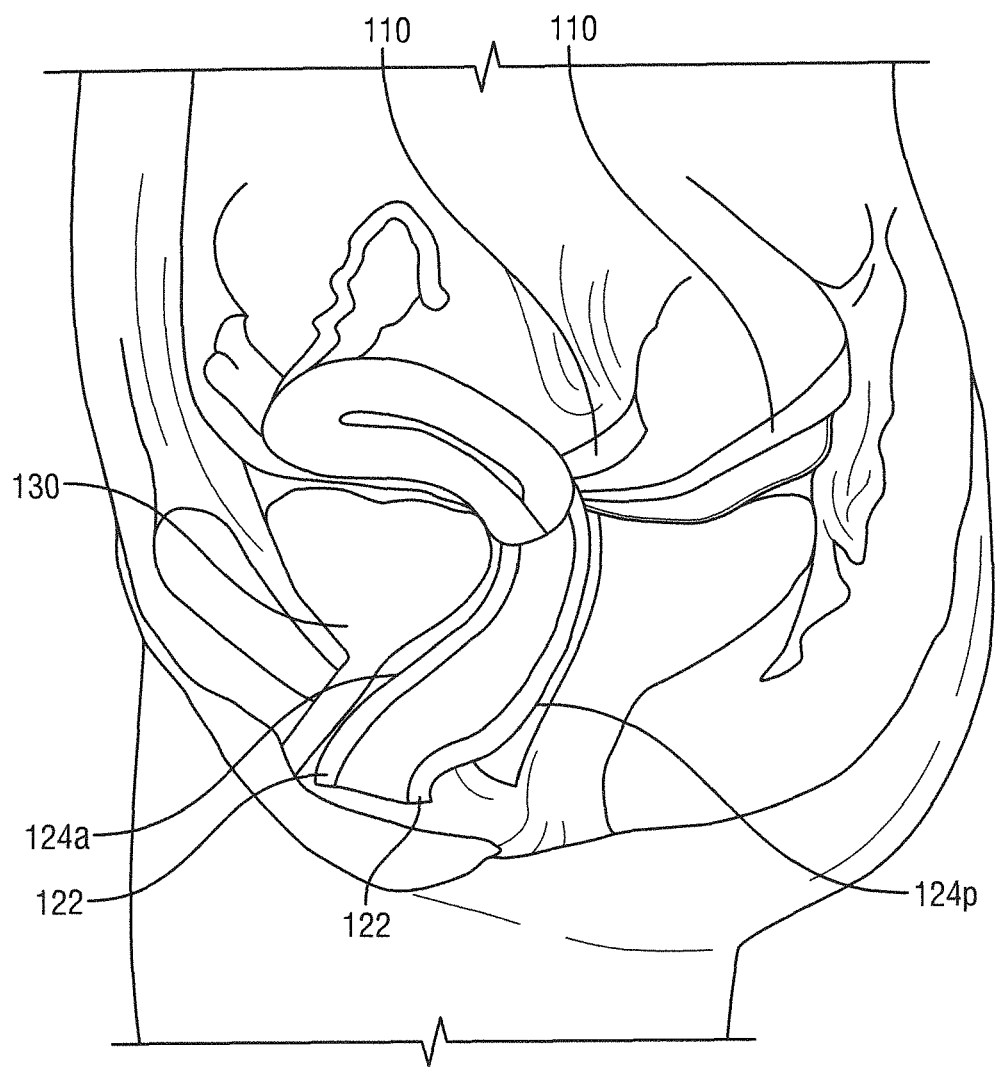
FIG. 1 is a schematic cross-sectional view of a portion of the female anatomy.

The present disclosure pertains to compositions, kits and methods of increasing tissue strength, including promoting tissue regeneration and/or remodeling in tissues, such as supporting tissues (e.g., ligaments, connective tissue, muscles, etc.) for pelvic organs, among others.

In accordance with one aspect, suitable compositions are injected into, applied onto or attached to support tissues of interest. For instance, as described in more detail below, one of the following procedures, or a combination of any two or all three of the following procedures, may be performed: (a) a suitable composition (e.g., a hydrogel, plug, etc.) may be injected into support tissue (e.g., a native ligament such as a uterosacral ligament, etc.) to promote remodeling of the support structure, another suitable composition (e.g., solid or solidifiable polymeric composition, etc.) may be applied onto the surface of the support tissue to temporarily or permanently increase the strength of the support tissue, and a further suitable composition (e.g., a graft) may be attached to the support tissue and also to another structure in the body (e.g., the vaginal apex, etc.).

Compositions may be injected into, applied onto or attached to support tissues of interest by one or more of the following routes, among others: via open abdominal surgery (laparotomy), laparoscopically, transvaginally (e.g., by vaginal incision), transrectally, transcystoscopically or percutaneously.

In some embodiments, a suitable solid or solidifiable composition is applied to the surface of a tissue of interest using a suitable application technique. For example, a suitable solid composition (e.g., in the form of a sheet or strip) may be attached or adhered to the tissue or a suitable solidifiable fluid composition may be applied onto the surface of the tissue, for example, by spraying, brushing, rolling, extruding or another suitable technique.

In some embodiments, a suitable composition is injected into tissue of interest such that an implant (e.g., a hydrogel implant or polymer composition implant) is formed in the tissue of interest. The composition may be injected at a single site, or in multiple sites as needed. For example, a hydrogel composition can be pre-formed ex vivo and injected into the tissue of interest, or a hydrogel precursor can be injected into the tissue of interest which subsequently forms a hydrogel composition in vivo, among other techniques. The hydrogel implant that is formed in the tissue promotes tissue regeneration and/or remodeling, leading to an increase in biomechanical strength of the tissue.

In some embodiments, a solid composition is injected into the tissue.

For example, one or more solid plugs containing tissue growth factors and/or other therapeutic agent can be injected into the tissue. The plug(s) may be injected at a single site, or in multiple sites as needed. The shape of the plug(s) may be varied. For example, the plug(s) may be in the form of one or more sharpened plugs which can be injected into the tissue (e.g., via a push rod or in the form of darts which can be injected into tissue, for example, by propelling the darts from a suitable device) or in the form of one or more fibers (which could, for example, be aligned in the tissue to direct tissue regrowth). Plug shapes include pellets, beads, cylinders or tubes, among others. The plugs can be any suitable size, e.g., from nanotube size to several millimeters in length and/or width as appropriate for the best repair. For example, the plugs may have a length and a width selected, independently, from sizes ranging 1 nm to 10 nm to 100 nm to 1 μm to 10 μm to 100 μm to 500 μm to 1 mm to 5 mm to 10 mm, among other values.

As used herein the term "hydrogel composition" embraces both preformed hydrogel compositions and hydrogel precursor compositions.

An "injectable" composition is a fluid, solidifiable or solid (e.g., plug) composition that can be delivered by injection (e.g., through a needle under pressure exerted using a syringe, via a push rod, propelled from suitable device, etc.).

A "solidifiable" composition is a composition that can be applied to a surface or below the surface in fluid form whereupon it solidifies through active or passive means into a solid material.

For ease of reference, a schematic cross-sectional view of a female human anatomy is shown in FIG. 1 and shows the bladder, rectum, uterus and urethra 130. Also shown are the vaginal epithelium 122 as well as the anterior vaginal wall 124a (pubocervical fascia) and the posterior vaginal wall 124p (rectovaginal fascia), which are part of the vaginal support structure. The two uterosacral ligaments (USLs) 110 are also shown, which are present on each side of the uterus and extend from the uterine cervix to the sacrum, serving to support the uterus and hold it in place.

In some embodiments, a suitable composition is applied onto and/or injected into native tissue (e.g., the USLs, the uterus in the areas where the USLs attach to the uterus, etc.) in order to increase tissue strength thereby preventing or retarding POP without the need for organ removal (e.g., removal of the uterus).

In other embodiments, a suitable composition is applied onto and/or injected into native tissue that is retained after organ removal (e.g., after uterus removal in a hysterectomy procedure) in order to increase tissue strength and improve the likelihood of success in the procedure.

For example, in patients where it is desired to attach the USLs to the vagina during a vaginal vault suspension procedure after hysterectomy, a suitable composition may be applied onto and/or injected into the USL, the vaginal support structure, or both. The support structure at the apex of the vagina includes the pubocervical fascia (anterior vaginal wall) and the rectovaginal fascia (posterior vaginal wall).

In specific embodiments, an injection device may be inserted through a working channel of a laparoscope, hysteroscope, cystoscope or other suitable endoscopic device for visual guidance, and a suitable composition injected at multiple points (e.g., multiple evenly spaced points) along each USL ligament. If desired, the composition may also be injected at multiple points (e.g., multiple evenly spaced points) along the anterior and posterior walls transvaginally (e.g., using the same injection device).

Injection devices for use in the present disclosure may comprise, for example, a proximal syringe, an elongated tube (catheter) and a distal needle, preferably with the syringe and needle engaging the catheter tube via suitable fittings (e.g., Luer fittings, etc.). In some embodiments, the injection device comprises an array of needles, allowing multiple sites to be injected simultaneously. In some embodiments, multiple injection devices may be employed. Beneficial needle sizes include 15-28 gauge needles (e.g., 15 to 16 to 17 to 18 to 19 to 20 to 21 to 22 to 23 to 24 to 25 to 26 to 27 to 28 gauge), more typically 20 to 25 gauge needles.

In specific embodiments, an application device may be inserted through a working channel of a laparoscope, hysteroscope, cystoscope or other suitable endoscopic device for visual guidance, and a suitable composition applied to the each USL ligament. If desired, the composition may be also applied to the anterior and posterior vaginal walls. For example, a suitable solid composition (e.g., in the form of a sheet or strip) may be attached to the tissue using a suitable coupling material such as a biodegradable or nonbiodegradable staple, biodegradable or nonbiodegradable suture or biodegradable or nonbiodegradable adhesive, among others. Alternatively, one or more solidifiable fluid compositions may be applied onto the tissue, for example, using a brush or roller or spray device, or dripped onto the surface or delivered through a catheter tube (e.g., via a proximal delivery device such as a syringe which may be coupled to the catheter tube via a suitable fitting such as a Luer fitting, etc.).

Figure 2:
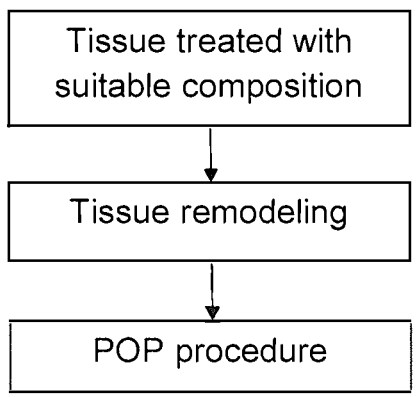
FIGS. 2-5 are flow charts schematically illustrating various methods in accordance with the invention.

In some embodiments, illustrated schematically in FIG. 2, suitable compositions may be applied onto and/or injected into tissue (e.g., USL, vaginal tissue, or both) at a point in time before POP procedure (e.g., before hysterectomy and vaginal vault suspension) that is sufficient to allow the tissue to regenerate by the time of the procedure.

Figure 3:
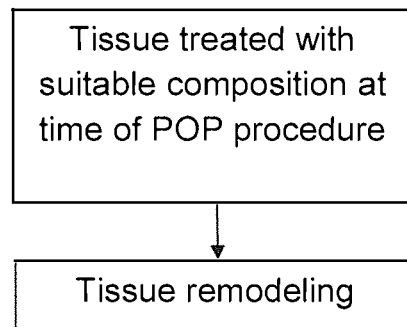

In other embodiments, illustrated schematically in FIG. 3, suitable compositions may be applied onto and/or injected into tissue (e.g., USL, vaginal tissue, or both) at the time of the POP procedure (e.g., immediately prior to a procedure combining hysterectomy and vaginal vault suspension), with tissue regeneration occurring subsequent to the procedure.

Figure 4:
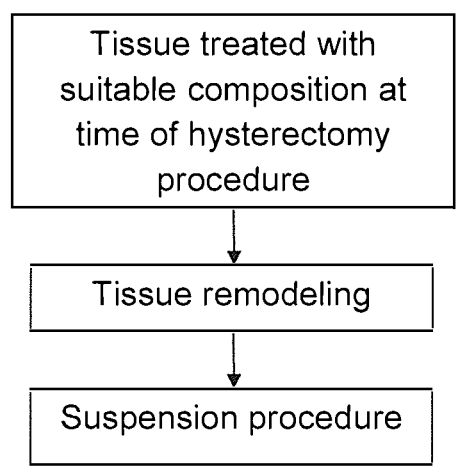

In other embodiments, suitable compositions may be applied onto and/or injected into tissue (e.g., USL, vaginal tissue, or both) at the time of the hysterectomy (e.g., immediately prior to uterus removal). Then, the tissue is left to regenerate/remodel and the wounds are allowed to heal for a time after the hysterectomy. If ligament repositioning is needed, a second surgery may be performed. For example, a USL suspension may be performed, during which the USL ligaments are sutured directly or indirectly to the vaginal walls to re-suspend the vagina. Such procedures are illustrated schematically in FIG. 4.

In certain cases, supporting tissue (e.g., ligaments, connective tissue, muscles, etc.) may be too damaged or torn for direct attachment to other living tissue. For example, the USLs may be too damaged or torn for direct attachment to vaginal tissue in a USL suspension procedure. In such cases, in addition to applying a suitable composition onto and/or injecting a suitable composition into the USLs, grafts (e.g., a synthetic graft, biologic graft or a combination synthetic/biologic graft) may be attached to the USLs.

Figure 5:
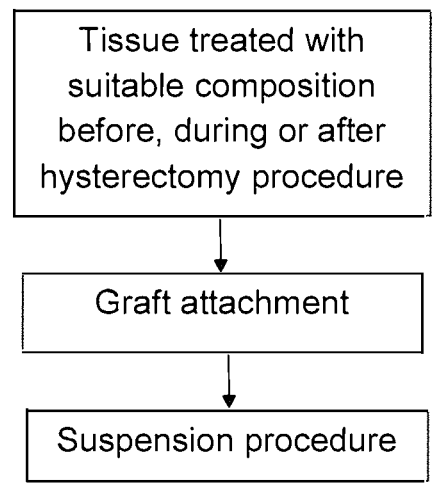

For instance, suitable compositions may be applied onto and/or injected into the USLs before, during or after removal of the uterus, and a graft may be attached to the USLs after removal of the uterus and before or after the introduction of the composition. This procedure is illustrated schematically in FIG. 5. In a particular instance, a suitable composition may be applied onto and/or injected into the USLs prior to removal of the uterus, and a graft may be attached to the USLs after removal of the uterus.

The graft may be attached to the USLs, for instance, by stapling (e.g., using biostable or bioabsorbable staples), suturing (e.g., using biostable or bioabsorbable sutures) or by use of a suitable biostable or biodegradable tissue adhesive.

The grafts may then be attached to vaginal tissue, either immediately, or after a period of healing and remodeling (i.e., during a second surgery). In one particular embodiment, a biologic graft is stapled, sutured or glued onto the USL ligaments and the two ligaments are connected by a synthetic graft material in the middle which is cut at the time of uterosacral ligament suspension procedure.

As previously indicated, visualization may be achieved during the procedures described herein using various devices, for example, using a laparoscope, hysteroscope, cystoscope or other suitable endoscope. Alternatively, a combination of two visualization devices may be used (e.g., an abdominally inserted laparoscope and a transvaginally inserted endoscope) to ensure appropriate visualization and access to USLs.

The injectable compositions, the solid or solidifiable compositions for application onto or into tissue, and/or the grafts described herein may contain suitable imaging agents as discussed below. For example, a biocompatible dye (e.g., fluorescent dye, colorimetric dye, etc.) may be employed in the injectable compositions to ensure that the injection sites are readily visualized during the procedure. A biocompatible dye may also be employed in solid or solidifiable compositions suitable for application onto or into tissue to ensure that the areas of application are readily visualized. A biocompatible dye may also be used to mark the graft material that is employed, if any. Where a fluorescent dye is employed, a scope (e.g., endoscope, laparoscope, etc.) may be used as a conduit for an optical fiber connected to a fluorescence optical system. As another example, injectable compositions, solid or solidifiable compositions suitable for application onto or into tissue, and/or grafts may also contain radiopaque agents to enable visualization via x-ray radiation. Such agents include barium sulphate, bismuth compounds, or tungsten, among others. The loading of such agents will be controlled to maximize contrast, while maintaining appropriate physical properties. For example, loadings of up to 20 or 30% by volume may be optimal, although for more dense agents, such as tungsten, the loading may be only 5% by volume.

In some embodiments, it is desirable to match the physical properties of the graft material and/or solid/solidified material with the physical properties of the USLs (e.g., the Young's modulus may be matched) to provide for more normal load bearing and to help stimulate proper cell growth and remodeling, for example, stimulation of fibroblasts to generate collagen, and proper conversion of collagen III to collagen I. The Young's modulus of the or solid/solidified material and grafts may range, for example, from 50 kPA to 1000 kPA (e.g., 50 kPA to 75 kPA to 100 kPA to 200 kPA to 300 kPA to 400 kPA to 500 kPA to 750 kPA to 1000 kPa), preferably, 400 kPA to 500 kPA in some embodiments.

As defined herein, a "biologic" material is a material that comprises one or more extracellular matrix components. Biologic materials for use in the grafts described herein include crosslinked and non-crosslinked allograft (e.g., human cadaveric) materials, as well as crosslinked and non-crosslinked heterograft (e.g., bovine, porcine, equine, etc.) materials. Specific examples of non-crosslinked biologic materials include mammalian non-crosslinked biologic matrix materials, such as human dermis, human fascia lata, fetal bovine dermis and porcine small intestinal submucosa. Specific examples of crosslinked biologic materials include mammalian crosslinked biologic materials such as crosslinked porcine dermis, crosslinked porcine small intestinal submucosa, crosslinked bovine pericardium, and crosslinked horse pericardium. Such materials are typically acellular. Moreover, they are typically predominantly formed of collagen.

Synthetic materials for use in the grafts described herein may be selected from biostable synthetic polymers, biodegradable synthetic polymers and combinations of biostable and biodegradable synthetic polymers.

As used herein, "polymers" are molecules that contain multiple copies of one or more types of constitutional species, commonly referred to as monomers. The number of monomers within a given polymer for use herein may vary widely, ranging, for example, from 2 to 5 to 10 to 25 to 50 to 100 to 1000 to 10,000 or more constitutional units. As used herein, the term "monomer" may refer to the free monomers and those that are incorporated into polymers (also referred to herein as monomer "residues"), with the distinction being clear from the context in which the term is used.

As used herein, "oligomers" are small polymers containing from 2 to 5 monomers.

Biostable synthetic polymers may be selected, for example, from the following, among others: (a) polyolefin homopolymers and copolymers, including homopolymers and copolymers of C2-C8 alkenes, for example, polyethylene and polypropylene among others, (b) fluoropolymers, including homopolymers and copolymers of C2-C8 alkenes in which one or more hydrogen atoms are substituted with fluorine, for example, polytetrafluoroethylene (PTFE), polyvinylidene fluoride (PVDF), poly(vinylidene fluoride-co-hexafluoropropene) (PVDF-HFP) among others, (c) polyamides such as nylons, among others, (d) polyesters, including, for example, polyethylene terephthalate, among others, (e) polyurethanes such as polyisobutylene based polyurethanes (PIB-PU) that comprise one or more polyisobutylene segments, among others, (f) polyoxyalkylenes including homopolymers of trioxane (polytrioxane, also known as polyoxymethylene or acetal) and copolymers of trioxane (e.g., copolymers of trioxane and dioxane), (g) styrenic copolymers such as alkene-styrene copolymers, including block copolymers comprising one or more polystyrene blocks and one or more polyalkene blocks, for instance, poly(styrene-b-isobutylene-b-styrene) (SIBS), poly(styrene-b-ethylene/butylene-b-styrene) (SEBS) among others, and (h) as well as various other polymers and copolymers (including block copolymers).

Biodegradable synthetic polymers may be selected, for example, from polyesters and polyanhydrides, among others. Specific biodegradable polymers may be selected from suitable members of the following, among others: (a) polyester homopolymers and copolymers (including polyesters and poly[ester-amides]), such as polyglycolide, polylactide (PLA), including poly-L-lactide, poly-D-lactide, and poly-D,L-lactide, poly(lactide-co-glycolide) (PLG), including poly(L-lactide-co-glycolide), poly(D-lactide-co-glycolide) and poly(D,L-lactide-co-glycolide), poly(beta-hydroxybutyrate), poly-D-gluconate, poly-L-gluconate, poly-D,L-gluconate, poly(epsilon-caprolactone), poly(delta-valerolactone), poly(p-dioxanone), poly(trimethylene carbonate), poly(lactide-co-delta-valerolactone), poly(lactide-co-epsilon-caprolactone), poly(lactide-co-beta-malic acid), poly(lactide-co-trimethylene carbonate), poly(glycolide-co-trimethylene carbonate), poly(beta-hydroxybutyrate-co-beta-hydroxyvalerate), poly[1,3-bis(p-carboxphenoxy)propane-co-sebacic acid], poly(sebacic acid-co-fumaric acid), and poly(ortho esters) such as those synthesized by copolymerization of various diketene acetals and diols, among others; and (b) polyanhydride homopolymers and copolymers such as poly(adipic anhydride), poly(suberic anhydride), poly(sebacic anhydride), poly(dodecanedioic anhydride), poly(maleic anhydride), poly[1,3-bis(p-carboxphenoxy)methane anhydride], and poly[alpha,omega-bis(p-carboxphenoxy)alkane anhydrides] such as poly[1,3-bis(p-carboxphenoxy)propane anhydride] and poly[1,6-bis(p-carboxphenoxy)hexane anhydride], among others.

Where a biodegradable polyester is used (e.g., PLA, PLG, etc.), one or more soft blocks, for example, polyethylene oxide (PEO), poly(trimethylene carbonate) (PTMC), poly(dioxane-2-one) (PPDO) or polycaprolactone (PCL) blocks, among others, may be included with one or more polyester blocks in the polymer to vary hardness, elongation, and degradation rate of the polymer. Examples include diblock and triblock copolymers such as PLA-PCL, PLA-PCL-PLA, PLG-PCL, PLG-PCL-PLG, PLA-PEO, PLA-PEO-PLA, PLG-PEO, PLG-PEO-PLG, PCL-PLA-PTMC, PLA-PTMC-PCL and PLA-PTMC-PPDO, among others.

Where copolymers are employed, copolymers with a variety of monomer ratios may be available. For example, where isobutylene-styrene copolymers (e.g., SIBS) are used, the ratio of monomers in these polymers can be selected to obtain mechanical properties such that tissue compatibility is enhanced. For instance, a higher isobutylene content will result in a softer polymer that may be a better match for the durometer of the surrounding tissue. As another example, where PLG is used, a variety of lactide:glycolide molar ratios will find use herein, and the ratio is largely a matter of choice, depending in part on the rate of degradation desired. For instance, a 50:50 PLG polymer, containing 50% D,L-lactide and 50% glycolide, will provide a faster resorbing copolymer, while 75:25 PLG degrades more slowly, and 85:15 and 90:10, even more slowly, due to the increased lactide component. Degradation rate can also be controlled by such factors as polymer molecular weight and polymer crystallinity. More broadly, where used, PLG copolymers include those having a lactide/glycolide molar ratio ranging, for example, from 10:90 or less to 15:85 to 20:80 to 25:75 to 40:60 to 45:55 to 50:50 to 55:45 to 60:40 to 75:25 to 80:20 to 85:15 to 90:10 or more.

In some cases, it may be desirable to support the vagina for a period after a surgical procedure is performed (e.g., 2-4 weeks) to promote healing. For instance, vaginal support device such as a biostable or biodegradable pessary may be inserted into the vagina for this purpose. A suitable pessary may be selected from a variety of vaginal pessary designs known in the obstetrics/gynecology art including ring pessaries (with or without knob), Shaatz pessaries, dish pessaries, oval pessaries, Gehrung pessaries, Gellhorn pessaries, Hodge pessaries, Risser pessaries, Smith pessaries, cube pessaries, cup pessaries, donut pessaries, and Marland pessaries, among others.

Inflatable devices may also be used to support the vagina after surgery. Inflatable devices may serve to provide a mechanical stimulus that promotes tissue regeneration. For instance, continuous expansion and contraction of a compliant balloon-inflatable device may allow tissue to be stretched and contracted during healing so that the tissue remodels appropriately. Some specific examples of suitable inflatable devices include inflatable pessary devices such as those described in U.S. Pat. No. 5,611,768 to Tutrone, Jr., U.S. Pat. No. 6,470,890 to Diokno et al., and Publication No. US 2009/0216071 to Zipper.

In other embodiments, a vaginal cap (e.g., a cap of hemispherical or other suitable geometry) may be applied to the vaginal apex to maintain the shape of the vaginal apex during healing. Such a cap may be held in place on the interior or exterior or the vaginal apex, for example, via a biodegradable adhesive, staple or suture. Such a cap may be formed, for example, from a suitable biodegradable and biostable material. For instance, a suitable biologic material, biostable synthetic polymer or biodegradable synthetic polymer selected from those described above may be employed.

As indicated above, compositions may be applied onto the surface of support tissue (e.g., ligaments, connective tissue, muscle, etc.) in solid or solidifiable form to temporarily improve (e.g., in the case of biodegradable compositions) or permanently improve (e.g., in the case of biostable compositions) the biomechanical strength of the tissue. For example, in some embodiments, a suitable composition in solid form may be contacted with the tissue and, if desired, secured in place, for instance, by a staple, suture or a suitable adhesive. In certain beneficial embodiments, the solid composition is microtextured to accommodate protein adhesion. In further embodiments, a solidifiable composition is applied onto the tissue in a fluid form, which solidifies after application onto the tissue, for example, due to removal of solvent from the composition or chemical curing (e.g., crosslinking) of the composition, among other mechanisms.

Compositions may also be injected into support tissue (e.g., ligaments, connective tissue, muscle, etc.) in solid or solidifiable form to promote tissue regeneration and/or remodeling in tissues. For example, in some embodiments, a suitable solid composition is injected into tissue in the form of a plug. As another example, in some embodiments, a suitable solidifiable composition is injected into the tissue in a fluid form, which solidifies after injection into the tissue, for example, due to removal of solvent from the composition or chemical curing (e.g., crosslinking) of the composition, among other mechanisms.

Solid and solidifiable compositions for application onto or into tissue include both biodegradable and biostable materials. For instance, in some embodiments, such solid and solidifiable compositions may contain one or more suitable biologic materials, biostable synthetic polymers or biodegradable synthetic polymers selected from those described above, among others.

In some embodiments, a suitable curable material such as a radiation curable material (e.g., a material curable with ionizing or non-ionizing radiation including e-beam radiation, gamma radiation, visible light, UV light, etc.) may be employed as a solidifiable composition. For example, radiation hydrogel curable hydrogel precursors such as those described below, among others, may be applied to tissue and cured. In some embodiments, a biodegradable or biostable synthetic adhesive (e.g., a cyanoacrylate adhesive, etc.), a biologically derived adhesive (e.g., a two-part fibrin glue), a moisture activated fibrin based powder, dextran based adhesive, serum albumin based adhesive, or other medical adhesives known to those in the art may be employed. One specific example, of a radiation curable material is a photopolymerized gelatin as described in as described in Elvin et al., "A highly elastic tissue sealant based on photopolymerised gelatin," Biomaterials 31 8323-8331 (2010).

As previously noted, in various embodiments, hydrogel compositions are beneficial for use as injectable compositions in accordance with the present disclosure and include both injectable preformed hydrogel compositions and injectable hydrogel precursor compositions.

As used herein, a "hydrogel" is a three-dimensional, crosslinked network comprising hydrophilic polymers that contain a substantial amount of water. A hydrogel may contain, for example, from 30 wt % to 40 wt % to 50 wt % to 60 wt % to 70 wt % to 80 wt % to 90 wt % to 95 wt %, or more, water on a w/w basis. A "hydrogel precursor" is a hydrophilic polymer (which may be an oligomer or a larger polymer) that is capable of becoming crosslinked to form a hydrogel.

Hydrogels may be physically crosslinked, chemically crosslinked, or both. Physically crosslinked hydrogels are formed by non-covalent interactions such as van der Waals forces, hydrophobic interactions, and/or electrostatic interactions (e.g., charge-charge interactions, charge-dipole interactions, and dipole-dipole interactions, including hydrogen bonding). Chemically crosslinked hydrogels are formed through covalent bonds.

Hydrogel precursors may become physically or chemically crosslinked in vivo in response to changes in various conditions, including temperature, pH and ionic strength or upon exposure to stimuli such as radiation (e.g., ionizing or non-ionizing radiation including e-beam radiation, gamma radiation, visible light, UV light, etc.) and magnetic fields. Thus, physical crosslinking commonly arises from self-assembly under stimuli that do not lead to covalent bond formation, including changes in temperature, pH, ion concentration, and hydrophobic interactions, among others. Chemical cross-linking may be obtained via photo-initiated, redox-initiated or Michael-type addition polymerization reactions, among others.

In some embodiments, a hydrogel may be formed (e.g., crosslinked) ex vivo and used to create a hydrogel composition which is introduced into the tissue of a subject. In such embodiments, the hydrogel composition may be further treated (e.g., by shearing, grinding, etc.) to provide a suitable injection consistency.

In other embodiments, a hydrogel precursor composition may be introduced into the tissue of a subject and crosslinked in vivo.

Hydrogels can be made from virtually any hydrophilic polymer. Hydrogels for use in the present invention thus include hydrogels formed from hydrophilic natural polymers, such as hydrophilic amino-acid-based polymers, including peptides (i.e., amino-acid polymers typically containing from 2 to 50 amino acids), proteins (i.e., amino-acid polymers typically containing more than 50 amino acids), and polyaspartamide, as well as polysaccharides, for instance, collagen, gelatin, fibrin, albumin, hyaluronic acid, glycosaminoglycans, alginates (including alginic acid and its derivatives), agarose, chitosan, cellulosic polymers such as carboxymethyl cellulose, starches including hydroxyethyl starch and dextran polymers including dextran and carboxymethyl dextran, among others. Hydrogels for use in the present invention also include hydrogels formed from hydrophilic synthetic polymers, for example, selected from polyethers including polyalkylene oxides such as polyethylene oxide (also referred to as polyethylene glycol), polypropylene oxide and polyethylene glycol-co-polybutylene terephthalate, polyols such as polyvinyl alcohol, polyacids such as polyacrylic acid, polymethacrylic acid and derivatives thereof, including polyacrylates, polymethacrylates such as poly(2-hydroxyethyl methacrylate) (which is also a polyol) and polyacrylamides including poly(N-isopropylacrylamide), polyamines, hydrolyzed polyacrylonitrile, poly(vinyl pyrrolidone), polyphosphazene, hydrophilic polyurethanes and synthetic hydrophilic polypeptides (e.g., polymers and copolymers of hydrophilic amino acids such as arginine, lysine, asparagine, glutamic acid, aspartic acid, and proline), among others.

In addition to water and polymer, hydrogel compositions in accordance with the invention may optionally include additional agents, as desired, including crosslinking species, therapeutic agents, imaging agents, tonicity adjusting agents, hydrogel particle suspension agents, biologically active agents, such as enzymes or peptides, and pH adjusting agents, among others.

Solid and solidifiable compositions for application onto or into tissue and grafts for use in the present disclosure may also contain crosslinking species, therapeutic agents, imaging agents, reinforcing agents, and cells (e.g. stem cells, mesenchymal cells, cells harvested from patient tissue including ligaments and other support tissue, etc.), among others.

Examples of therapeutic agents for use herein include biologic agents that stimulate fibroblast activity including proteins such as FOX03A and Hox-A11, Lysil oxidase (LOX), proteoglycans, glycosaminoglycans, and growth factors such a fibroblast growth factor (FGF), hormones such as estrogen, progesterone, and progesterone diol, and other wound healing agents such as NO-releasing compounds. Examples of NO-releasing compounds include O-nitroso compounds (e.g., compounds having one or more —O—NO groups), S-nitroso compounds (e.g., compounds with one or more —S—NO groups) and N-nitroso compounds (e.g., compounds having an =N—NO group, for instance, compounds having —N—$N_2O_2^-$ groups, which are known as N-nonoate compounds). NO-donors may be covalently coupled with a polymer such as poly(vinyl alcohol), among other polymers described herein.

Examples of imaging agents include (a) fluorescent dyes such as fluorescein, indocyanine green, or fluorescent proteins (e.g. green, blue, cyan fluorescent proteins), (b) contrast agents for use in conjunction with magnetic resonance imaging (MRI), including contrast agents that contain elements with relatively large magnetic moment such as Gd(III), Mn(II), Fe(III) and compounds (including chelates) containing the same, such as gadolinium ion chelated with diethylenetriaminepentaacetic acid, (c) contrast agents for use in conjunction with ultrasound imaging, including organic and inorganic echogenic particles (i.e., particles that result in an increase in the reflected ultrasonic energy) or organic and inorganic echolucent particles (i.e., particles that result in a decrease in the reflected ultrasonic energy), and (d) contrast agents for use in connection with x-ray fluoroscopy, including metals and metal compounds (e.g., metal salts, metal oxides, etc.), for instance, barium compounds, bismuth compounds and tungsten, among others, and iodinated compounds, among others. As noted above, the loading of such agents will be controlled to maximize contrast, while maintaining appropriate physical properties. For example, loadings of 5 vol % or less to 30 vol % or more may be employed (e.g., 5 vol % to 10 vol % to 15 vol % to 20 vol % to 25 vol % to 30 vol %).

If in vivo elution of an imaging agent (e.g., dye) is of concern, the agent may be covalently attached to the compositions described herein, or particles containing the agent may be included in the compositions. In a specific embodiment, microparticles or nanoparticles containing the agent may be attached to parts of the graft, or smaller removable parts of the graft may be employed that contain imaging agents (e.g., enough area to allow for visualization).

Examples of initiators include photoinitiators (benzoin ethers, aryl ketones, acyl phosphine oxides, etc.), thermal initiators (as peroxide initiators, azo initiators, etc.), and redox initiators. Also included in the formulation can be catalysts, accelerators, hardening agents, and so forth.

Examples of crosslinking species further include, for example, multifunctional crosslinking agents having two or more reactive groups, such as crosslinking agents having two or more sites of unsaturation (e.g., —HC=CH—, —HC=CH$_2$, —C≡C— or —C≡CH), two or more epoxide groups, two or more glycidyl groups, two or more carboxylic acid groups, di-aldehydes, disulfides, diimidazoles, diimides, and diisocyanates, among others.

An advantage of using hydrogel precursors is that crosslinking (e.g., photocrosslinking, etc.) may be conducted at the time of administration or may be postponed to ensure that the newly introduced material has been first accepted by the tissue. In this regard, reports have indicated that crosslinked collagen grafts result in encapsulation in vaginal tissue while non-crosslinked collagen is well integrated (see, e.g., Claerhout et al., "Fate of collagen-based implants used in pelvic floor surgery: A 2-year follow-up study in a rabbit model," American Journal of Obstetrics and Gynecology 198 94.el (2008)).

To achieve in vivo cross-linking of a photocrosslinkable composition such as a photocrosslinkable hydrogel precursor composition among other photocrosslinkable compositions, light can be introduced to the delivery site (e.g., to the site where the composition is injected or applied), for example, by insertion of a light-transmitting optical fiber through a scope (e.g., a laparoscope or a suitable endoscope positioned in an incision in the vagina, etc.), among other methods.

Where curable compositions (e.g., radiation curable compositions including photocrosslinkable compositions and chemically curable compositions including moisture curable and two-part systems) are employed, curing times will vary with the curable composition selected and may range widely, for example, preferably ranging from 5 seconds to 8 hours (e.g., from 5 seconds to 10 seconds to 15 seconds to 30 seconds to 1 minute to 2 minutes to 5 minutes to 10 minutes to 30 minutes to 1 hour to 2 hours to 4 hours to 8 hours), more preferably from 10 seconds to 5 minutes.

Examples of tonicity adjusting agents for use in the hydrogel compositions of the present disclosure include sugars (e.g., dextrose, lactose, etc.), polyhydric alcohols (e.g., glycerol, propylene glycol, mannitol, sorbitol, etc.) and inorganic salts (e.g., potassium chloride, sodium chloride, etc.), among others.

Examples of suspension agents for use in the hydrogel compositions of the present disclosure include various surfactants, wetting agents, and polymers (e.g., albumin, PEO, polyvinyl alcohol, block copolymers, etc.), among others.

Examples of pH adjusting agents for use in the hydrogel compositions of the present disclosure include various buffer solutes.

Specific examples of suitable hydrogels for use in the hydrogel compositions of the present disclosure include hydrogels based on polyethylene glycol, dextran and/or hyaluronic acid (HA), among others.

For example, U.S. Patent Pub. No. 2010/0055184 to Zeitels et al., describes polymeric hydrogel comprising a semi-interpenetrating network of a cross-linked polymer and a water soluble polymer. Water soluble polymers described include polyethylene glycol, poly(lysine), hyaluronic acid, dextran, alginate, gelatin, elastin, collagen, cellulose, methylcellulose, and derivatives thereof Crosslinked polymers described include cross-linked diacrylate polymers, specifically, cross-linked polyethylene glycol diacrylate. Cross-linking is preformed ex vivo using a UV light (200-400 nm) in the presence of an aryl ketone photoinitiator, specifically 4-(2-hydroxyethoxy)phenyl-(2-hydroxy-2-propyl)ketone (Irgacure 2959). Elastic shear modulus is adjusted by forcing the hydrogel through a series of needles with smaller and smaller bores.

A hydrogel of this type, specifically, a semi-interpenetrating network of cross-linked polyethylene glycol diacrylate (PEG-DA) and polyethylene glycol (PEG) in a 3:7 ratio of PEG-DA to PEG (30 wt % PEG-DA) has been employed by Zeitels and others to treat canine vocal cords. See Sandeep S. Karajanagi et al., "Assessment of Canine Vocal Fold Function After Injection of a New Biomaterial Designed to Treat Phonatory Mucosal Scarring," Ann Otol Rhinol Laryngol 2011; 120: 175-184. The material is referred to by the authors as PEG30.

Another PEG hydrogel, this one based on polyethylene glycol (PEG) and hyaluronic acid (HA), is described in A. T. Hillel et al., "Photoactivated Composite Biomaterial for Soft Tissue Restoration in Rodents and in Humans," Sci. Trans'. Med. 3, 93ra67 (2011). In this work, a photo-crosslinkable, injectable hydrogel precursor composition comprising PEG-DA, HA and a suitable photoinitiator system (eosin Y) was injected into dermal tissue and subsequently subjected to transdermal light exposure to achieve crosslinking See also U.S. Patent Pub. No. 2011/0002997 to Elisseeff et al.

An advantage of using a combination of two polymers (e.g., PEG diacrylate and another water soluble polymer such as PEG or HA, among others) in a hydrogel composition is the ability to tune the mechanical properties (e.g., elasticity, etc.) within the tissue by varying the ratio of the two polymers.

Crosslinked HA hydrogels have also been used in the restoration of vocal folds. See X. Jia et al., "Hyaluronic acid-based microgels and microgel networks for vocal fold regeneration, "Biomacromolecules 7 (2006) 3336-44, in which HA microgels were prepared by cross-linking HA derivatives carrying hydrazide (HAADH) and aldehyde (HAALD) functionalities within inverse emulsion droplets; as an alternative, poly(ethylene glycol) dialdehyde (PEG-DiALD) was employed in place of HAALD. Other forms of crosslinked HA hydrogels include auto-crosslinked HA hydrogels. As described in Davide Renier et al., "Pharmacokinetic behaviour of ACP gel, an autocrosslinked hyaluronan derivative, after intraperitoneal administration," Biomaterials 26 (2005) 5368-5374, auto-cross-linked HA derivatives may be obtained through a cross-linking process that results in condensation and, therefore, does not require bridge molecules. The chemical functions that contribute to the cross-linking process are carboxyl groups, and hydroxyl groups and/or amine groups. The reaction is begun by activating some of the carboxyl groups using a suitable condensing agent followed by nucleophilic attack by the hydroxyl or amine groups, creating an ester-type or amide-type bond which may involve the chain of hyaluronic acid itself (intramolecular crosslink) as well as other chains. Id.

Dextran hydrogels may also be used in the hydrogel compositions of the present disclosure. One exemplary hydrogel is a dextran hydrogel prepared at John Hopkins University, known to enhance wound healing and tissue regeneration in deep skin burn injuries with no additional growth factors, cytokines, or cells. G. Sun et al., "Dextran hydrogel scaffolds enhance angiogenic responses and promote complete skin regeneration during burn wound healing" PNAS, Dec. 27, 2011, vol. 108, no. 52, 20976-20981.

In addition, polyacrylamide hydrogels may also be used in the hydrogel compositions of the present disclosure. Polyacrylamide hydrogels have been used in restoration of dermal tissue. For example, Aquamid®, from Contura International A/S, Soeborg, Denmark, is an injectable hydrogel composition consisting of 97.5% water and 2.5% cross-linked polyacrylamide. U.S. Pat. No. 7,790,194, assigned to Contura, describes a polyacrylamide gel manufactured by a polymerization of the monomers of acrylamide and N,N'-methylene-bis-acrylamide, more specifically, a system based on acrylamide monomer, N,N'-methylene-bis-acrylamide monomer (as crosslinker), ammonium persulfate free-radical initiator, and N,N,N',N'-tetramethylene ethylene diamine (TMED) co-initiator. The resulting gels are purified and homogenized by grinding.

Gelatin may also be used in the hydrogel compositions of the present disclosure. For example, a composition comprising gelatin, ruthenium catalyst and a persulphate oxidant may be employed in a system analogous to that described in Elvin et al., "A highly elastic tissue sealant based on photopolymerised gelatin," Biomaterials 31 8323-8331 (2010). Covalent di-tyrosine crosslinks can be formed by exposure to blue light, either ex vivo or in vivo. As with various other photocrosslinkable compositions described herein, the hydrogel may be formed ex vivo, or a precursor composition may be administered and crosslinked in vivo.

In another aspect of the disclosure, kits useful in treating a patient in need of tissue repair are provided. The kits may include all or a subset of all the components useful for treating a patient.

The kits may include, for example, materials compositions that are ready for application onto or injection into patient tissue. For example, the kits may contain solid materials in the form of sheets or strips for application to patient tissue or plugs for injection into patient tissue. The kits may contain one or more containers of a solidifiable material (e.g., a material that solidifies upon temperature change, solvent evaporation, crosslinking, etc.) which may be administered onto or into patient tissue as described herein. The kits may contain one or more containers of a hydrogel composition that is ready for application onto or injection into patient tissue.

The kits may contain one or more containers of material that is used to form an administrable composition ex vivo or in vivo. For example, the kits may contain one or more containers of a composition in dry form (e.g., a hydrogel composition) that is ready for administration upon addition of a suitable liquid carrier. The kits may contain one or more containers of precursor materials (e.g., hydrogel precursor materials), for instance, one or more containers of a cross-linkable composition (e.g., one comprising a multifunctional crosslinkable polymer and/or monomer) in wet or dry form. The kits may contain one or more containers of hydrogel precursor material in fluid form that may be exposed to radiation (in vivo or ex vivo) to form a hydrogel. The kits may contain one or more containers of hydrogel precursor material in dry form which is first hydrated (e.g., using a suitable carrier) and then exposed to radiation to form a hydrogel. As another example, the kits may contain separate containers of (a) crosslinkable material such as a hydrogel precursor in wet or dry form and (b) a cross-linking reagent (e.g., initiator, catalyst, accelerator, etc.) in wet or dry form, or the kits may contain separate containers containing components of a two-part curing system.

The kits may also contain one or more containers of anesthetics, antibiotics, growth factors, and/or other active agents in wet or dry form.

The kits may include one or more containers of a suitable liquid carrier (e.g. sterile water for injection, physiological saline, phosphate buffer, a solution containing an imaging contrast agent, etc.) which may be used to reconstitute materials in dry form.

The kits may include a device or receptacle for preparation of compositions including hydrogel compositions, for example, a measuring or mixing device.

The kits may include injection devices for administering compositions to tissue. Exemplary injection devices include specialized syringes, needles, and catheters that are compatible with a variety of scope designs (endoscope, laparoscope, etc.); the injection device may be designed with one needle or multiple needles (e.g., in a linear or non-linear array) to simultaneously inject compositions into multiple sites. The kits may also include application devices for administering fluid compositions onto tissue surfaces, for example, brushes, rollers, sprayers and catheter tubes that are compatible with a variety of scope designs (endoscope, laparoscope, etc.). In some embodiments, the kit includes a catheter tube and syringe which can be coupled to the catheter tube via a suitable fitting, such as a Luer fitting.

The kits may further contain a curing system such as a UV lamp or a fiber optic which is coupled to a UV source or is configured to be coupled to be to a UV source. Such curing systems may be employed ex vivo. Such curing systems may also be employed in vivo, in which case such systems can be made compatible with a variety of scope designs (endoscope, laparoscope, etc.).

The kits may include grafts, such as synthetic grafts, biologic grafts or combination synthetic/biologic grafts.

The kits may contain securement materials such as staples, suture materials and/or adhesive compositions such as tissue adhesives. The kits may also contain other devices designed to hold the composition in place during cure.

The kits may contain one or more devices such as vaginal pessaries or inflatable devices (including inflatable pessaries) for support of the vaginal vault after surgery. The kits may contain one or more devices such as caps for maintaining the shape of the vaginal apex after surgery.

The kits may include instructions for administering the materials contained in the kits (e.g., compositions for application onto tissue, compositions for injection into tissue, grafts, staples, sutures, adhesives, pessaries, caps, etc.). The kits may also include packaging and information as required by a governmental regulatory agency that regulates pharmaceuticals and/or medical devices.

In certain embodiments, the components of the kits are provided in a sterile package for convenient use by a health care professional. In certain embodiments, the kits may provide the necessary components for a single use, include various components selected from those described above, for example, combinations of two or more of the following: (a) one or more containers of an injectable composition as described herein, (b) one or more packages or containers of solid or solidifiable materials as described herein, (c) one or more administration devices as described herein (e.g., injection devices, catheters, sprayers, rollers, brushes, etc.), (d) a source of radiation (e.g., a UV lamp, fiber optic cable, etc.), (e) a vaginal support device (e.g., a vaginal pessary, inflatable device, cap, etc.), (f) graft material, and (g) securement material (e.g., sutures, staples, adhesives, etc.), among other components.

In certain embodiments, the kits can contain biological or chemical therapeutic agents that can be loaded into the compositions on site. Alternatively, the practitioner can select biological or chemical agents as appropriate for loading at the time of the procedure.

Although various embodiments are specifically illustrated and described herein, it will be appreciated that modifications and variations of the present invention are covered by the above teachings and are within the purview of any appended claims without departing from the spirit and intended scope of the invention. For example, the kits and compositions of the present invention may be used in medical procedures other than procedures for remodeling ligaments, connective tissue, muscles and organs (e.g., USL, vagina, uterus, etc.) of the pelvis, including other ligaments, connective tissue, muscles and organs throughout the body. Such compositions may be administered, for example, to the bladder (e.g., to address bladder cancer, interstitial cystitis, overactive bladder, etc.), rectum, and urethral and anal sphincters (e.g., to address incontinence, etc.), among many other applications.

The invention claimed is:

1. A surgical procedure comprising delivering an injectable hydrogel composition onto and/or into pelvic tissue to provide support to the pelvic tissue, wherein the injectable hydrogel composition comprises a polysaccharide.

2. The surgical procedure of claim 1, wherein the injectable hydrogel composition is delivered percutaneously.

3. The surgical procedure of claim 1, wherein the injectable hydrogel composition is delivered through a needle under pressure exerted using a syringe.

4. The surgical procedure of claim 3, wherein the needle is a 16 to 22 gauge needle.

5. The surgical procedure of claim 1, wherein the pelvic tissue comprises muscle tissue.

6. The surgical procedure of claim 1, wherein the pelvic tissue comprises the rectum.

7. The surgical procedure of claim 1, wherein the polysaccharide comprises one or more of a glycosaminoglycan, chitosan, hyaluronic acid, dextran, alginic acid and hydroxyethyl starch.

8. The surgical procedure of claim 1, wherein the polysaccharide comprises hyaluronic acid.

9. The surgical procedure of claim 1, wherein the injectable hydrogel composition comprises an additional agent selected from crosslinking species, therapeutic agents, imaging agents, tonicity adjusting agents, hydrogel particle suspension agents, and pH adjusting agents.

10. The surgical procedure of claim 1, wherein the injectable hydrogel composition comprises a contrast agent to enable visualization.

11. The surgical procedure of claim 1, wherein the injectable composition comprises a therapeutic agent selected from a growth factor, a wound healing agent or both.

12. The surgical procedure of claim 1, wherein the injectable hydrogel composition injected at multiple points.

13. A surgical procedure comprising delivering an injectable hydrogel composition onto and/or into pelvic tissue to provide support to the pelvic tissue, wherein the injectable hydrogel composition comprises hyaluronic acid, wherein the injectable hydrogel composition is delivered through a needle under pressure exerted using a syringe.

14. The surgical procedure of claim 13, wherein the injectable hydrogel composition is delivered percutaneously.

15. The surgical procedure of claim 14, wherein the needle is a 16 to 22 gauge needle.

16. The surgical procedure of claim 13, wherein the pelvic tissue comprises muscle tissue.

17. The surgical procedure of claim 13, wherein the pelvic tissue comprises the rectum.

* * * * *